United States Patent
Herve et al.

(10) Patent No.: US 6,808,691 B1
(45) Date of Patent: Oct. 26, 2004

(54) SEALABLE STERILIZING PACKAGING MATERIAL

(75) Inventors: Philippe Herve, Reynes (FR); Agnes Paris-Jolly, Voreppe (FR)

(73) Assignee: Arjo Wiggins, Issy-Les-Moulineaux (FR)

( * ) Notice: Subject to any disclaimer, the term of this patent is extended or adjusted under 35 U.S.C. 154(b) by 0 days.

(21) Appl. No.: 09/555,525

(22) PCT Filed: Oct. 12, 1998

(86) PCT No.: PCT/FR99/02455

§ 371 (c)(1),
(2), (4) Date: Aug. 8, 2000

(87) PCT Pub. No.: WO00/21745

PCT Pub. Date: Apr. 20, 2000

(30) Foreign Application Priority Data

Oct. 12, 1998 (FR) ............................................. 98 12753

(51) Int. Cl.⁷ ................................................ A61L 2/00
(52) U.S. Cl. .................... 422/294; 53/128.1; 53/453; 206/329; 206/363; 206/439; 422/297; 422/300
(58) Field of Search .............................. 53/128.1, 453; 422/294, 297, 300; 206/363, 439, 329

(56) References Cited

U.S. PATENT DOCUMENTS 4,714,595 A * 12/1987 Anthony et al. ............ 422/294
4,724,961 A    2/1988 Shimoyamada et al.
5,246,109 A *  9/1993 Markle et al. .............. 206/363
5,418,022 A *  5/1995 Anderson et al. .......... 428/35.2
5,730,530 A    3/1998 Stoddard et al.

FOREIGN PATENT DOCUMENTS

WO     WO 96 16562 A     6/1996

OTHER PUBLICATIONS

Database WPI, Section Ch, Week 9005, Derwent Publications Ltd., London, XP002112231.

* cited by examiner

Primary Examiner—Krisanne Jastrzab
(74) Attorney, Agent, or Firm—Bacon & Thomas

(57) ABSTRACT

A sealable sterilising material for packaging medical devices requiring sterilization, has an average burst strength not less than 200 kPa measured according to ISO 2758 standard, an average tear strength not less than 300 mN measured according to the European standard 21974, an average impact strength not less than 0.4 J measured according to the ASTM standard and a bacterial filtering efficiency (BFE) not less than 85%, with a basic weight ranging between 40 and 250 g/m², preferably between 90 and 250 g/m², measured according to the ISO 536 standard and includes at least two sterilising packaging sheets (F1) and (F2), one of them at least being sealable directly or after being coated with a sealing product. The sheets are bound irreversibly together by one of their surfaces. The invention also concerns a package made from the material.

26 Claims, No Drawings

SEALABLE STERILIZING PACKAGING MATERIAL

The present invention relates to a sealable sterilizing packaging material for medical devices that have to be sterilized as well as to the sterilizing package itself.

Sealable sterilizing packages for medical devices that have to be sterilized, especially reusable instruments or devices, such as probes, scalpels, clamps, scissors and needles, are already known.

In fact, to sterilize the medical devices, it is possible to use a heat- and/or pressure-sealable sterilizing package which may be a flexible or semi-rigid package, in the form of a sachet, a bag, a sheath or a blister pack, or else a rigid package.

The rigid package is a container consisting of a receptacle, generally made of plastic and thermoformed, which will contain the medical devices to be sterilized and which will then be closed by a cover which may be a sealable sheet of paper acting as a barrier to microorganisms. This sheet is a barrier sheet similar to that used for the other type of package described below.

The flexible or semi-rigid package in the form of a sachet, a bag, a sheath or a blister pack is a package consisting of a part (1), which may be made of synthetic material, and of a sheet of paper (2) having a specific permeability, these being sealed together along a certain perimeter according to the shape desired for the package, a relatively large opening being left so as to introduce the articles. The articles to be sterilized are placed inside the package and then the said package is completely sealed. The part (1) made of synthetic material may be a thermoplastic film such as polyethylene or polypropylene film. This film is generally impermeable to gases and to steam and, in addition, is transparent so as to see the contents of the package. Instead of the plastic film, it is also possible to use a sheet similar to the sheet of paper (2) which has a specific permeability or a sheet of paper coated with a sealing product such as a layer of extruded polyethylene or of poly(vinyl acetate). In the case of a blister pack, a flexible plastic film, thermoformed to the shape of the device to be packaged, is used.

The sheet of paper (2) has a specific permeability which makes it a barrier to microorganisms but which allows the sterilizing agents to pass through it so as to sterilize the closed package and its contents by sterilization methods using, as sterilizing agents, steam or sterilizing gases such as ethylene oxide. The package may also be sterilized by ionizing radiation, such as gamma or beta rays.

Advantageously, these packages offer the possibility of individually packaging the articles and of being opened, if necessary, only at the moment the sterilized article is used. They therefore allow the sterilized articles to be stored under proper sterility conditions.

In more detail, the sheet of paper (2) that can be used to form these packages is obtained via a wet route using a paper process by dewatering an aqueous suspension of cellulose fibres which generally includes a wet-strength agent. In addition, a cohesion agent may be introduced either throughout the aqueous suspension of fibres or by a surface treatment of the wet sheet, in order to mechanically strengthen the sheet. Moreover, a sizing agent may also be introduced either throughout the aqueous suspension of fibres or by a surface treatment of the wet sheet, so as to reduce the absorption of water by the sheet. Next, the sheet is dried.

This sheet may be coated on one of its sides, uniformly, with a continuous layer, or in patterns, especially patterns of grids or zones, with a heat-and/or pressure-sealing adhesive. It is then sealed against a plastic film or another sheet of paper acting as a barrier to microorganisms, over a certain perimeter depending on the desired shape of the package, while leaving an opening. In some cases, the sheet of paper is not coated with such an adhesive since, because its composition includes a compound having heat-sealing properties, such as starch for example, or else a thermoplastic polymer which is in the form of fibres or is introduced in the form of a stable aqueous emulsion (latex), it may be heat-sealed directly against a thermoplastic film. The packages are cut to the suitable shape and size.

The specific permeability of these sheets of paper is obtained by the choice of cellulose pulps, generally comprising between 0 and 70% by weight of short fibres and the balance to 100, of long fibres, of their refining (unrefined to a refining of 40 degrees Schoepper-Riegler) and by adjustments to the paper machine that are known to those skilled in the art. The entanglement of fibres of the sheet allows there to be a compromise between the porosity of the sheet and the diameter of the pores which creates this necessary specific permeability and a tortuous path in order not to let the molecules of water vapour or of sterilizing gases to penetrate without letting them pass over the dust particles carrying bacteria or other microorganisms. In the field of sealable sterilizing packages, it is recommended that a mean equivalent pore diameter not exceed 35 $\mu$m and no individual diameter value exceed 50 $\mu$m, according to the BS 3321:1986 standard.

British Patent Application GB 1,559,843 has described a sterilizing bag formed on one side from an impermeable thermoplastic film (1) and on the other side by a sheet of paper/impermeable thermoplastic film complex (3) sealed to a sheet of paper (2) acting as a barrier to bacteria and being permeable to the sterilizing agents (gases or steam), the complex being shorter in length than the other constituents so that the sterilizing agents can penetrate that region of the sheet (2) which remains permeable. The purpose of the construction of this package is to protect the sterilized articles when opening the bag. In particular, it prevents particles which could be pulled out the sheet of paper (2) when opening the package from being deposited on the articles. However, it has the drawback that its manufacture is not very practical since it requires having to join sheets of different length together and the sterilizing agents can penetrate only a small region, a situation which may be prejudicial to proper sterilization.

Moreover, sheets for sealable sterilizing packages are known which are based only on cellulose fibres (no synthetic fibres) and are manufactured and sold by Arjo Wiggins under the trademarks ETHYPEL® and PROPYPEL® in Europe. These sheets form a high bacterial barrier but have a mechanical strength which may prove to be insufficient, even if they are surface treated with a strengthening agent such as starch, polyvinyl alcohol or an acrylic latex, when it is desired to package heavy or sharp articles.

Paper sheets reinforced by synthetic fibres mixed with the cellulose fibres have therefore been proposed. For example, such sheets comprising polyester synthetic fibres are sold by Argo Wiggins under the trademark STERISHEET® in Europe. For an equivalent grammage, these so-called reinforced sheets have a higher mechanical strength than purely cellulosic sheets but, on the other hand, their bacterial barrier is slightly lower.

Other sterilizing packaging sheets have also been proposed which are sheets of nonwovens obtained by a dry route and comprising only hot-bonded synthetic fibres. For example, such sheets made of polyethylene fibres are sold by DuPont de Nemours under the trademark TYVEK®. These sheets have a high mechanical strength. However, one drawback with these sheets is that their look-through is very heterogeneous, that is to say the distribution of the fibres is very irregular and therefore the permeability of the sheet is not uniform. Thus, at certain points, the sheet may have pores too large in diameter. These purely synthetic sheets also have the drawback of having extremely long biodegradability times. Moreover, they are more expensive.

What is therefore sought is a sterilizing packaging sheet which has simultaneously and necessarily several properties.

One of the properties is that the sheet must be tear resistant. This is because, as it is intended for making packages which will contain articles that may be heavy or sharp, it risks being torn or pierced by these articles when handling the said packages. In the case of a sealable sterilizing package, it is desirable to have a mean tear strength greater than 300 mN measured according to European Standard EN 21974.

Another mechanical property is that the sheet must be burst resistant. This is because, while the packages are being sterilized, it may be subjected to a pressure during injection of the sterilizing gases and to a high vacuum subsequently, during removal of the gases which must be complete. In the case of a sealable sterilizing package, it is desirable to have a burst strength not less than 200 kPa measured according to the standard ISO 2758.

In addition, another mechanical property of the sheet is its impact strength. In the case of a sealable sterilizing package, it is desirable to have a strength, characterized by its resistance to the impact of a pendulum defined according to the standard ASTM D3420, which is not less than 0.40 Joule.

Another property is that the sheet must be permeable to the sterilizing agents. This is because, as described above, when the article has been introduced into the package and the latter has then been sealed, the assembly is subjected to the action of sterilizing gases or of steam. In the case of a sealable sterilizing package, it is desirable to have an air permeability measured according to the standard ISO 5363-3, Bendtsen method, greater than 0.2 $\mu$m/(Pa.s).

However, another property is that the sheet must be a barrier to bacteria or other microorganisms in order to maintain the sterility of the package, that is to say microorganisms must not be able to penetrate the inside of the package after sterilization. It is therefore necessary for the mean of the largest pore diameters not to be too great and for no pores to have too large a diameter. This barrier property may be characterized by bacterial filtering efficiency usually referred to by the initials of its English term BFE (Bacterial Filtration Efficiency); it is expressed as a percentage which represents the percentage of bacteria stopped by the sheet. In the case of a sealable sterilizing package, it is desirable to have a BFE of at least 85%.

Another property of this sheet is that it must be sealable either because of its composition or because it is able to receive a sealing layer.

Another desirable property of these sheets is that they allow aseptic opening of the package after sterilization. Such opening means that, when the sterilized package is opened, no fibres or other particles from the sheet become detached and deposited on the sterilized articles. To achieve this, the package must be opened without tearing the sheet. The sheets are referred to as being peelable.

Another desirable property of the package obtained is that the sealing forces must be high enough to prevent the package from opening adventitiously. Therefore, the heavier the devices to be sterilized, the higher the sealing force of the package must be, so that the package does not open owing to their weight. However, the more this force is increased, the higher the risks of the sheet tearing when opening it. It is therefore necessary for the sheet also to have a very high surface cohesion and/or internal cohesion in order for there to be proper aseptic opening.

It is therefore necessary for the sterilizing packaging sheets to be mechanically strong while being permeable to sterilizing gases and acting as barriers to microorganisms.

By increasing the grammage of the sheets, it is possible to improve some of these properties, without however obtaining the combination of all the desired properties, and in addition this increases their cost. is Moreover, if it is attempted to reinforce the surface of the sheets, in order to have greater cohesion for example, by impregnating it with a reinforcing product, its structure is opened up and its bacterial filtering efficiency is reduced. Tests carried out on the sheet of Comparative Example 5 mentioned later have demonstrated this fact.

The problem is therefore to provide a sterilizing packaging sheet which has the abovementioned required properties, in particular which has both a very high overall mechanical strength and a high microbial barrier, and this being so while minimizing its grammage.

The Applicant has discovered that, by irreversibly bonding two sterilizing packaging sheets together via one of their sides, especially by pasting, a material is obtained which solves the problem since it has all the desired properties and, in addition, the said material is in every way superior to a simple sterilizing packaging sheet having the same grammage as the said material.

Thus, the invention provides a sealable sterilizing packaging material for medical devices that have to be sterilized, having a mean burst strength not less than 200 kPa measured according to the standard ISO 2758, a mean tear strength not less than 300 mN measured according to the European Standard EN 21974, a mean impact strength not less than 0.4 J measured according to the standard ASTM D 3420 and a bacterial filtering efficiency BFE not less than 85%, having a grammage ranging between 40 and 250 g/m$^2$, preferably between 70 and 250 g/m$^2$, measured according to the ISO 536 standard and comprising at least two sheets of sterilizing packaging (F1) and (F2), at least one of the sheets being sealable directly or after being coated with a sealing product, the said sheets being irreversibly bonded together via one of their sides.

The fact that the two sheets are bonded together irreversibly means that the two sheets cannot be separated without at least one of them being torn, that is to say the bond strength between the two sheets is greater than the lower of the cohesion strengths of the sheets.

Preferably, the material according to the invention has a bacterial filtering efficiency BFE not less than 90% and even more preferably not less than 95%.

More particularly, the invention provides a material which is characterized in that the two sheets of sterilizing packaging (F1) and (F2) are bonded together by bonding points such that the said bonding points are in a discrete form at the bonding interface of the sheets.

Preferably, the material is characterized in that the discrete bonding points are uniformly distributed at the interface of the sheets.

The sheets (F1) and (F2) may be bonded together by any technique allowing the material resulting from joining the sheets to have a high permeability to the sterilizing agents and a high barrier to microorganisms. Consequently, the interface of the joined sheets must not be too obstructing. It may be any technique allowing discrete bonding points to be made between the sheets, such as hot bonding using high-frequency radio waves or ultrasonic waves, or using a suitable means, for depositing an adhesive or else by using a porous adhesive.

According to a preferred embodiment of the invention, the material is characterized in that the sheets (F1) and (F2) are bonded together by an adhesive.

According to one particular embodiment of the invention, the adhesive is deposited by a coating process using halftone gravure printing, that is to say the printing cylinder is etched with uniformly spaced cells or cells in a grid or in other patterns.

The adhesive may be a paste normally used in the paper-pasting field, such as starch or certain polymers used in the form of a stable aqueous emulsion such as, in particular, polyacrylates, polyurethanes and styrene-butadiene copolymers, these optionally being carboxylated; it may be a pressure-sensitive adhesive (PSA) or a hot-melt adhesive.

Thus, according to one particular embodiment of the invention, the adhesive is chosen from pressure-sensitive adhesives.

According to another particular embodiment of the invention, the adhesive is chosen from hot-melt adhesives, also called hot-melts.

According to one particular embodiment of the invention, the adhesive is a self-sealing adhesive, particularly natural rubber.

In fact, an adhesive such as natural rubber, or 1,4-cis-polyisoprene, can advantageously be used, this having the particular feature of sticking to itself only and therefore enabling sheets coated with it to be easily wound. Two sheets thus already coated may then be bonded together in line on the manufacturing machine, particularly a paper machine, without having subsequently to deposit an adhesive by bringing the coated side of a sheet against the coated side of the other sheet. The sheets may be joined together on the manufacturing machine if it has the suitable equipment.

According to one particular embodiment of the invention, the adhesive is a porous adhesive. This porous adhesive may be prepared by creating pores in a known adhesive either by a chemical reaction which produces a gas, before, during or after deposition of the adhesive, or by injecting an inert gas or air into the adhesive before or during its deposition on one of the sheets.

In addition, the adhesive, like all the other constituents of the material, must be selected on non-toxicity criteria given the end-use of the material, by relying, for example, on the standard ISO 10993-5 relating to the characterization of non-cytotoxicity of a material.

This adhesive may have both characteristics of an adhesive and also a mechanically reinforcing character for the sheets and therefore for the material.

The adhesive may be deposited on the surface of one of the sheets or of each of the sheets.

The amount of adhesive deposited will be as little as possible but must ensure permanent bonding between the sheets under conditions associated with the end-use of the material, particularly after having undergone sterilization.

Preferably, the amount of adhesive deposited will range between 1 and 20 g/m$^2$ and more particularly between 5 and 10 g/m$^2$.

The sheet (F1) may be a sheet obtained by a papermaking route, comprising only cellulose fibres, the fibres possibly being modified such as rayon fibres resulting from the sodium hydroxide treatment of viscose or regenerated cellulose fibres in solvent medium, such as those sold under the brand names LYOCELL® or TENCEL®, as a mixture with a wet strength agent and a paper strengthening agent added into the bulk or on the surface, such as a polyvinyl alcohol, a starch or a oolymer added in the form of a stable aqueous emulsion (latex), especially acrylic polymers or acrylates.

The sheet (F1) may also be a sheet obtained by a papermaking route comprising cellulose fibres, possibly modified like the rayon fibres coming from the sodium hydroxide treatment of viscose, or regenerated cellulose fibres in solvent medium, such as those sold under the trademarks LYOCELL® or TENCEL®, as a mixture with synthetic fibres, all these fibres being bonded either by thermal bonding or by water-jet bonding, or chemically by means of the addition in bulk, or by means of a surface treatment such as in a sizing press or by spraying, of a binder normally used in papermaking such as a polyvinyl alcohol, a starch or a polymer added in the form of a stable aqueous emulsion (latex). In particular, the synthetic fibres are in amounts ranging between 5 and 95 parts by dry weight, the total sum of the fibres making 100 parts.

Thus, the invention provides a material which is characterized in that the sheet (F1) is a paper sheet and in that it comprises:

between 5 and 100 parts by weight of cellulose fibres, the cellulose possibly being modified;

between 0 and 95 parts by weight of synthetic fibres, the sum of the cellulose fibre parts and the synthetic fibre parts making 100;

between 0 and 5% of a wet-strength agent by dry weight of the total composition of the sheet;

between 0 and 40% of a cohesion agent by dry weight of the total composition of the sheet.

The sheets may optionally be creped, microcreped or embossed when dry. They may be coloured or tinted.

It is also possible to use sheets having only synthetic fibres, particularly of the nonwoven type, however those having, at least partly, cellulose fibres are preferred since they have better biodegradability.

The sheet (F2) may be a sheet obtained by a papermaking route, comprising only cellulose fibres, possibly modified like the rayon fibres coming from the sodium hydroxide treatment of viscose, or regenerated cellulose fibres in solvent medium, such as those sold under the trademarks LYOCELL® or TENCEL®, as a mixture with a wet-strength agent.

The sheet (F2) may also be a sheet having the same compounds as the sheets (F1) described above, preferably with, as synthetic fibres, microfibres which give a superior level of microbial filtration.

In particular, the invention provides a material which is characterized in that the sheet (F2) is a paper sheet and in that it comprises:

between 90 and 100 parts by weight of cellulose fibres, the cellulose possibly being modified;

between 0 and 10 parts by weight of synthetic fibres, the sum of the cellulose fibre parts and synthetic fibre parts making 100;

between 0 and 5% of a wet-strength agent by dry weight of the total composition of the sheet;

between 0 and 40% of a cohesion agent by dry weight of the total composition of the sheet.

Preferably, the synthetic fibres are chosen from fibres of homopolymers or copolymers of olefins, of polyester, of polyamide and blends thereof. These fibres may also be two-component fibres having a core and a shell differing in chemical nature and/or having different properties, such as, for example, their melting points. These fibres may be chopped fibres.

The synthetic fibres preferably have a length ranging between 1 and 30 mm and, moreover, a linear density ranging between 0.4 and 5 dtex.

According to one particular embodiment of the invention, the cohesion agent is also the adhesive for bonding between the sheets (F1) and (F2).

The material obtained may then be used to make sealable packages intended for the sterilization of medical devices using operations known in this field, for example like those explained above in the description of the prior art.

Thus, the invention provides a sealable sterilizing package for medical devices that have to be sterilized, which is characterized in that it comprises the said sterilizing packaging material.

In particular, the invention provides a package which is characterized in that the sheet (F2) having the greater bacterial filtering efficiency BFE is located on the outside of the package.

According to one particular embodiment, the invention provides a package which is characterized in that it consists of the said sterilizing material and a film of gas-impermeable thermoplastic polymer which is sealed against the said material over part of its perimeter.

According to another particular embodiment, the invention provides a package which is characterized in that it consists of the said sterilizing material sealed against itself or a sheet of paper coated with a sealing product such as a layer of extruded polyethylene or of poly(vinyl acetate).

According to another particular embodiment, the invention provides a package which is characterized in that it consists of a rigid container and of a cover formed by the said sterilizing material.

Although the invention preferably relates to the bonding of two sheets, it is not limited to the use of only two sheets, a person skilled in the art knowing how to adapt the grammages and characteristics of the various sheets according to the general teaching of the present description.

The invention will be more clearly understood with the help of the non-limiting examples according to the invention and of the comparative examples described below.

EXAMPLE 1 ACCORDING TO THE INVENTION

Production of a Packaging Sheet (F1):

The sheet is produced on a Fourdrinier paper machine. Cellulose fibres and polyester synthetic fibres in respective proportions of 90 parts and 10 parts by dry weight are put into suspension in aqueous medium. The cellulose fibres are a mixture of 20% by weight of short fibres and a balance to loo of long fibres, the fibres being refined to 25° SR. The polyester fibres have a length ranging between 5 and 25 mm and a linear density of 1.7 dtex. Added to this suspension are 0.26% by dry weight of the total composition of the sheet of a wet-strength agent of the PAE (polyamine epichlorohydrin) and 1% by dry weight of the total composition of the sheet of a cationic starch as internal cohesion agent.

This suspension is dewatered on the wire of the machine in order to form the sheet.

The sheet is impregnated in a sizing press with an acrylic synthetic cohesion agent introduced in the form of a stabilized aqueous emulsion. This acrylic agent is present in an amount of 8 g/m$^2$ by dry weight.

The sheet is dried at about 120° C.

The sheet then has a grammage of 47.4 g/m$^2$.

Production of a Packaging Sheet (F2):

The sheet is produced on a Fourdrinier paper machine. Cellulose fibres are put into suspension in aqueous medium. The cellulose fibres are a mixture of 20% by weight of short fibres and of its balance to 100 (i.e. 80%) of long fibres, the fibres being refined to 25° SR. Added to this suspension are 0.26% by dry weight of the total composition of the sheet of a wet-strength agent of the PAE (polyamine epichlorohydrin) type, 0.15% by dry weight of the total composition of the sheet of a sizing agent of the so-called AKD (alkyl ketene dimer) type and 1% by dry weight of the total composition of the sheet of a cationic starch as internal cohesion agent.

This suspension is dewatered on the wire of the machine in order to form the sheet.

The sheet is impregnated in a sizing press with a water-soluble cohesion agent which is a starch. This agent is present in an amount of 0.5 g/m$^2$ by dry weight of the total composition of the sheet.

The sheet is dried at around 120° C.

The sheet then has a grammage of 61.3 g/m$^2$.

Pasting of the Sheets (F1) and (F2) in Order to Form the Material According to the Invention:

A paste based on vinyl copolymers in aqueous medium is deposited on one side of one of the sheets. The paste is deposited in an amount of 5.3 g/m$^2$ by a coating system using halftone gravure printing. The two sheets manufactured beforehand are bonded together by passing them through rollers. The sheet is dried at around 150° C.

The material obtained is reeled up.

The grammage of the material is 114 g/m$^2$.

Production of the Sterilizing Package

The material is coated on one side of the sheet (F1) by gravure printing, with a heat-sealing lacquer based on a vinyl acetate-ethylene copolymer in aqueous medium, in an amount of 4 g/m$^2$ by dry weight. The coated material is dried and reeled up.

The coated material and a thermoplastic film of polyethylene are joined together by heat-sealing on a sealer-cutter so as to form bags sealed on three sides with one side open. The bags are then cut up. The bags may be used to sterilize medical devices that will be introduced thereinto.

EXAMPLE 2 ACCORDING TO THE INVENTION

Production of a Packaging Sheet (F1):

The sheet is produced on a Fourdrinier paper machine. Cellulose fibres are put into suspension in aqueous medium. Added to this suspension are 0.26% by dry weight of the total composition of the sheet of a wet-strength agent of the PAE (polyamine epichloro-hydrin) type, 0.10% by dry weight of the total composition of the sheet of a sizing agent of the so-called AKD (alkyl ketene dimer) type and 1% by dry weight of the total composition of the sheet of a cationic starch as internal cohesion agent.

This suspension is dewatered on the wire of the machine in order to form the sheet.

The sheet is impregnated in a sizing press with an acrylic synthetic cohesion agent introduced in the form of a stabilized aqueous emulsion. This acrylic agent is present in an amount of 8 g/m² by dry weight.

The sheet is dried at around 120° C.

The sheet then has a grammage of 42.4 g/m².

Production of a Packaging Sheet (F2): The same packaging sheet (F2) as in Example 1 is produced.

Pasting of the Sheets (F1) and (F2) in Order to Form the Material According to the Invention:

A paste based on vinyl copolymers in aqueous medium is deposited on one side of one of the sheets. The paste is deposited in an amount of 10.3 g/m² by a coating system using halftone gravure printing. The two sheets manufactured beforehand are bonded together by passing them through rollers. The sheet is dried at around 150° C.

The material obtained is reeled up.

The grammage of the material is 114 g/m².

Production of the Sterilizing Package: a Package as in Example 1 is Produced.

EXAMPLE 3

Production of a Packaging Sheet (F1):

The sheet is produced on a Fourdrinier paper machine. Cellulose fibres are put into suspension in aqueous medium. Added to this suspension are 0.26% by dry weight of the total composition of the sheet of a wet-strength agent of the PAE (polyamine epichloro-hydrin) type, 0.12% by dry weight of the total composition of the sheet of a sizing agent of the so-called AKD (alkyl ketene dimer) type and 1% by dry weight of the total composition of the sheet of a cationic starch as internal cohesion agent.

This suspension is dewatered on the wire of the machine in order to form the sheet.

The sheet is impregnated in a sizing press with an acrylic synthetic cohesion agent introduced in the form of a stabilized aqueous emulsion. This acrylic agent is present in an amount of 4 g/m² by dry weight.

The sheet is dried at around 120° C.

The sheet then has a grammage of 45.4 g/m².

A microcreping of the sheet is then produced by creping it dry.

Production of a Packaging Sheet (F2): The sheet (F2) described in Example 1 is repeated.

Pasting of the Sheets (F1) and (F2) in Order to Form the Material According to the Invention:

The sheets (F1) and (F2) are bonded together as in Example 2 with a 6.3 g/m² amount of paste deposited.

COMPARATIVE EXAMPLE 4

This example consists of a sterilizing packaging sheet intended to be coated with a sealing product, which comprises, to our knowledge, purely cellulose fibres and a high level of polymer introduced in the form of an aqueous dispersion (latex) both throughout the sheet and on its surface. This sheet is manufactured and sold with a grammage of 115 g/m² by the company Kimberly-Clark.

COMPARATIVE EXAMPLE 5

A sheet is produced on a Fourdrinier paper machine. Cellulose fibres are put into suspension in aqueous medium. Added to this suspension are 0.26% by dry weight of the total composition of the sheet of a wet-strength agent of the PAE (polyamine epichloro-hydrin) type, 0.17% by dry weight of the total composition of the sheet of a sizing agent of the so-called AKD (alkyl ketene dimer) type and 1% by dry weight of the total composition of the sheet of a cationic starch as internal cohesion agent.

This suspension is dewatered on the wire of the machine in order to form the sheet.

The sheet is impregnated in a sizing press with a mixture of starch and bonding agent.

This mixture is present in an amount of 1 g/m² by dry weight.

Its grammage is 115 g/m².

RESULTS

The measurements carried out according to the methods explained below, on the specimens of Examples 1, 4 and 5, are given in Table 1 and those for Examples 2 and 3 in Table 2. The permeability of the sheet (F1) of Example 3 is not given since in this sheet, being creped, the permeability cannot be determined using the Bendtsen method.

These results show that, on the one hand, the bacterial barrier efficiency and, on the other hand, the overall mechanical strength and in particular the impact strength as well as the tear strength are superior in the case of the materials according to the invention than in the case of simple sterilizing packaging sheets of the same grammage.

In particular, in Table 1, the physical and bacteriostatic properties of the sheets and materials of Examples 1, 4 and 5, before and after gamma-ray sterilization, are given.

The specimen to be tested was exposed to a $^{60}$Cobalt source, this being a source of so-called gamma ionizing radiation. The specimen received an absorbed radiation dose of 50 kGy. It is known that the properties are reduced by the radiation sterilization, particularly in the case of cellulose-based products, nevertheless Table 1 shows that the complex according to the invention retains properties at acceptable levels.

EXAMPLES 6 TO 10

Pasted materials of different grammages, between 70 and 260 g/m², are produced in the same way as that described in Example 1, using sheets F1 and F2 having, respectively, the compositions of those of Example 1 but with variable grammages. The amount of paste for the pasting is almost constant and is approximately 5.5 g/m² by dry weight. The physical and bacteriostatic properties of the sheets F1 and F2 and of the materials F1/F2 obtained are given in Table 3.

This Table 3 shows that all the properties in the case of the material F1/F2 are higher than the properties of the base sheets and, in particular, it may be seen that the tear strength is markedly improved.

EXAMPLES 11 to 14

Pasted materials with a given grammage are produced in the same way as that described in Example 1, using sheets F1 and F2 having, respectively, the compositions of those of Example 1 and the amount of paste deposited varied between 1.5 and 20 g/M² by dry weight.

The physical and bacteriostatic properties of the sheets F1 and F2 and of the materials F1/F2 obtained are given in Table 4.

This Table 4 shows that all the properties in the case of the material F1/F2 are higher than the properties of the base sheets and, in particular, it may be seen that the tear strength is markedly improved.

CHARACTERIZATION METHODS

The sheets (F1) and (F2) and the materials obtained were characterized by the methods referred to below.

Apart from the BFE, the measurements were made on specimens conditioned according to European Standard EN 20187 (equivalent to the standard ISO 187: 1995) in which the temperature must be maintained at 23° C. and the relative humidity at 50%.

adhesive-tape pull-out resistance test. This test is carried out by applying an adhesive tape having a width of between 1.27 and 1.90 cm to the sheet F1 side of the F1/F2 complex. The adhesive tape is sealed at 116° C. and at a pressure of 278 kPa for 2 seconds. The tape is left to cool and then peeled off at a constant rate at an angle of 180 degrees. The pulling-out of the particles onto the adhesive tape is assessed visually.

TABLE 1

| | Gamma sterilization | Grammage g/m$^2$ | Burst strength kPa | Tear strength mN | Impact strength J | Air permeability μm/(Pa · s.) | Pore diameter μm | Bacterial filtering efficiency BFE % | Pull-out resistance rating |
|---|---|---|---|---|---|---|---|---|---|
| Comparative Example 4 | Before | 115 | 350 | 824 | 0.39 | 6.8 | 28 | 97.3 | slight pull-out |
| | After | 109.6 | 303 | 620 | 0.30 | 7.80 | 25.1 | 97.0 | no pull-out |
| | % Variation | −4.7 | −13.4 | −24.8 | −23.8 | 15.0 | −10.4 | −0.31 | |
| Comparative Example 5 | Before | 115 | 570 | 1610 | 0.38 | 2.4 | 11 | 99.5 | extensive pull-out |
| | After | 116.2 | 349 | 1000 | 0.32 | 2.30 | 10.6 | 99.3 | extensive pull-out |
| | % Variation | 1.0 | −38.8 | −37.9 | −15.8 | −3.0 | −3.6 | −0.20 | |
| Sheet F1 of Example 1 | Before | 47.4 | 189 | 515 | 0.23 | 64.7 | 49.3 | 89.8 | slight pull-out |
| | After | 49 | 128 | 380 | 0.14 | 58.0 | 51.6 | 89.0 | slight pull-out |
| | % Variation | 3.4 | −32.3 | −26.2 | −38.3 | −10.4 | 4.7 | −0.89 | |
| Sheet F2 of Example 1 | Before | 61.3 | 332 | 650 | 0.34 | 8.6 | 26.1 | 95.3 | extensive pull-out |
| | After | 62 | 217 | 480 | 0.20 | 7.90 | 25 | 96.2 | extensive pull-out |
| | % Variation | 1.1 | −34.5 | −26.2 | −42.4 | −8.1 | −4.2 | 0.94 | |
| Example 1, material F1/F2 | Before | 114 | 609 | 1330 | >0.60 | 2.4 | 21.4 | 99.5 | no pull-out |
| | After | 115 | 414 | 1060 | 0.46 | 3.0 | 19.3 | 99.2 | no pull-out |
| | % Variation | 0.9 | −40.5 | −20.3 | N.A. | 25.0 | −9.8 | −.03 | |

The measurements are the mean of the measurements made on each side of the specimens.

The grammage is determined according to the International Standard ISO 536.

The mean tear strength (in the machine direction and in the cross direction) is measured according to European Standard EN 21974, which corresponds to International Standard ISO 1974: 1990 (Elmendorf method).

The mean dry burst strength is measured according to the ISO 2758 standard.

The mean pendulum impact strength is expressed as a fracture energy determined according to the American Standard ASTM D3420 on an apparatus of the SPENCER brand with a pendulum 800. When the limiting value that can be determined by the equipment is reached, the wording "greater than" is given in the table.

The mean air permeability is measured according to the ISO 5636/3 standard (Bendtsen method). This method does not apply to the creped sheets.

The mean equivalent pore diameter is measured according to the British Standard BS 3321: 1986.

The bacterial filtering efficiency BFE is determined according to the method published by the United States Association EDANA under the reference 180.0–89 of February 1996.

The proper cohesion of the material in order to have aseptic openability (peelability) is determined by the

TABLE 2

| | EXAMPLE 2 | | | EXAMPLE 3 | | |
|---|---|---|---|---|---|---|
| | Sheet F1 | Sheet F2 | Material F1/F2 | Sheet F1 | Sheet F2 | Material F1/F2 |
| Grammage (g/m$^2$) | 42.4 | 61.3 | 114 | 45.4 | 61.3 | 113 |
| Burst strength (kpa) | 200 | 331.5 | 480 | 150 | 331.5 | 405.6 |
| Tear strength (mN) | 400 | 650 | 1250 | 440 | 650 | 1214 |
| Impact strength (J) | 0.21 | 0.34 | >0.590 | 0.210 | 0.344 | 0.439 |
| Air permeability [(μm/(Pa.s.)] | 37.7 | 8.6 | 1.58 | — | 8.6 | 3.1 (smooth side) |
| Pore diameter (μm) | 36 | 26.1 | 21.9 | 40.4 | 26.1 | 23.9 |
| Bacterial filtering efficiency "BFE" (%) | 90.1 | 95.3 | 99.6 | 86.1 | 95.3 | 98.9 |
| Pull-out resistance test | | No pull-out | | | No pull-out | |

TABLE 3

|  | Paste g/m² | Grammage g/m² | Burst strength kPa | Tear strength mN | Impact strength J | Air permeability μm/(Pa · s) | Pore diameter μm | BFE efficiency % | Pull-out resistance rating |
|---|---|---|---|---|---|---|---|---|---|
| Sheet F1 | — | 47.4 | 189 | 515 | 0.23 | 65 | 49.3 | 66.0 | N.A. |
| Sheet F2 | — | 46.5 | 163 | 355 | 0.116 | 2.2 | 17.2 | 85.0 | N.A. |
| Material F1/F2 | 1.5 | 9.5 | 412 | 1030 | 0.46 | 1.30 | 15.7 | 98.1 | no pull-out |
|  | 6 | 101 | 410 | 1075 | 0.47 | 1.09 | 9.8 | 99.2 | no pull-out |
|  | 12 | 107 | 437 | 1030 | 0.55 | 0.80 | 10.2 | 99.8 | no pull-out |
|  | 20 | 111 | 463 | 1040 | 0.51 | 0.30 | 8.3 | 99.9 | no pull-out |

TABLE 4

|  | Grammage g/m² | Burst strength kPa | Tear strength mN | Impact strength J | Air permeability μm/(Pa · s) | Pore diameter μm | BFE efficiency % | Pull-out resistance rating |
|---|---|---|---|---|---|---|---|---|
| Sheet 1 | 30.0 | 65 | 341 | 0.084 | 106 | 164.5 | 34.0 | fibre pull-out |
| Sheet 2 | 34.7 | 106 | 312 | 0.093 | 40 | 60.7 | 58.0 | fibre pull-out |
| Material F1/F2 | 70.2 | 288 | 884 | 0.27 | 1.84 | 31.4 | 93.0 | no pull-out |
| Sheet 1 | 40.9 | 106 | 416 | 0.122 | 94 | 80.8 | 61.0 | fibre pull-out |
| Sheet 2 | 44.2 | 168 | 419 | 0.15 | 16 | 46.9 | 79.0 | fibre pull-out |
| Material F1/F2 | 89.9 | 431 | 1132 | 0.38 | 1.73 | 17.1 | 99.6 | no pull-out |
| Sheet 1 | 53.3 | 159 | 585 | 0.182 | 31 | 48.5 | 77.0 | fibre pull-out |
| Sheet 2 | 60.5 | 246 | 610 | 0.231 | 6.1 | 27.6 | 94.0 | fibre pull-out |
| Material F1/F2 | 119.3 | 561 | 1658 | >0.60 | 1.82 | 13.2 | 99.5 | slight pull-out |
| Sheet 1 | 82.6 | 298 | 870 | 0.231 | 9.1 | 30.2 | 93.0 | fibre pull-out |
| Sheet 2 | 95.3 | 458 | 1087 | 0.308 | 4.1 | 17.2 | 99.2 | fibre pull-out |
| Material F1/F2 | 183.4 | 935 | 2605 | >0.60 | 1.76 | 11.7 | 99.8 | very slight pull-out |
| Sheet 1 | 121.0 | 484 | 1505 | 0.441 | 5.3 | 21.8 | 99.3 | slight pull-out |
| Sheet 2 | 134.6 | 765 | 1695 | 0.528 | 3.2 | 12.1 | 99.9 | slight pull-out |
| Material F1/F2 | 260.6 | 1433 | 4691 | >0.65 | 1.70 | 11.5 | 99.9 | no pull-out |

What is claimed is:

1. Sealable sterilizing packaging material for medical devices that have to be sterilized, having a mean burst strength not less than 200 kPa measured according to the ISO 2758 standard, a mean tear strength not less than 300 mN measured according to the European Standard EN 21974, a mean impact strength not less than 0.4 J measured according to the standard ASTM D 3420 and a bacterial filtering efficiency BFE not less than 85%, having a grammage ranging between 40 and 250 g/m² measured according to the ISO 536 standard and comprising at least two sterilizing packaging sheets (F1) and (F2), at least one of the sheets being sealable directly or after being coated with a sealing product, the said sheets being irreversibly bonded together via one of their sides.

2. Material according to claim 1, characterized in that the two sheets of sterilizing packaging (F1) and (F2) are bonded together by bonding points such that the said bonding points are in a discrete form at the bonding interface of the sheets.

3. Material according to claim 1, characterized in that the discrete bonding points are uniformly distributed at the interface of the sheets.

4. Material according to claim 1, characterized in that the sheets (F1) and (F2) are bonded together by an adhesive.

5. Material according to claim 4, characterized in that the adhesive is chosen from pressure-sensitive adhesives.

6. Material according to claim 4, characterized in that the adhesive is chosen from hot-melt adhesives, also called hot-melts.

7. Material according to claim 4, characterized in that the adhesive is a self-sealing adhesive.

8. Material according to claim 4, characterized in that the adhesive is a porous adhesive.

9. Material according to claim 4, characterized in that the amount of adhesive deposited ranges between 1 and 20 g/m².

10. Material according to claim 4, characterized in that the adhesive is deposited by halftone gravure printing.

11. Material according to claim 1, characterized in that one of the sheets (F1) is sealable directly or after it has been coated with a sealing product and the other sheet (F2) has a bacterial filtering efficiency BFE not less than that of the sheet (F1) and in that this bacterial filtering efficiency BFE ranges between 80 and 100%.

12. Material according to claim 1, characterized in that the sheet (F1) is a paper sheet and in that it comprises:
   between 5 and 100 parts by weight of cellulose fibres, the cellulose fibers optionally being rayon fibres resulting from sodium hydroxide treatment of viscose or regenerated cellulose fibres in solvent medium;
   between 0 and 95 parts by weight of synthetic fibres, the sum of the cellulose fibre parts and the synthetic fibre parts making 100;
   between 0 and 5% of a wet-strength agent by dry weight of the total composition of the sheet;
   between 0 and 40% of a cohesion agent by dry weight of the total composition of the sheet.

13. Material according to claim 1, characterized in that the sheet (F2) is a paper sheet and in that it comprises:
   between 90 and 100 parts by weight of cellulose fibres, the cellulose fibers optionally being rayon fibres resulting from sodium hydroxide treatment of viscose or regenerated cellulose fibres in solvent medium;
   between 0 and 10 parts by weight of synthetic fibres, the sum of the cellulose fibre parts and synthetic fibre parts making 100;
   between 0 and 5% of a wet-strength agent by dry weight of the total composition of the sheet;
   between 0 and 40% of a cohesion agent by dry weight of the total composition of the sheet.

14. Material according to claim 12, characterized in that the synthetic fibres are chosen from fibres homopolymers or copolymers of polyolefins, of polyester, of polyamide.

15. Material according to claim 12, characterized in that the synthetic fibres have a mean length ranging between 1 and 30 mm and a mean linear density ranging between 0.5 and 5 dtex.

16. Material according to claim 12, characterized in that the cohesion agent is chosen from starches, polyvinyl alcohols, acrylicoracrylate polymers.

17. Material according to claim 12, characterized in that the cohesion agent is an adhesive selected from the group consisting of pressure sensitive adhesives, hot-melt adhesives, self-sealing adhesive, natural rubber adhesive, and porous adhesive.

18. Material according to claim 1, characterized in that said material is covered on one of its sides with a sealing adhesive uniformly distributed either continuously over its entire surface or in patterns of grids or zones.

19. Sealable sterilizing package for medical devices that have to be sterilized, characterized in that said package comprises said sterilizing material according to claim 1 configured as a package.

20. Package according to claim 11, characterized in that the sheet (F2) having the greater bacterial filtering efficiency BFE is located on the outside of the package.

21. Package according to claim 19, characterized in that said package consists of the said sterilizing material and a film of gas-impermeable thermoplastic material which is sealed against the said material over at least part of its perimeter.

22. Package according to claim 19, characterized in that it consists of the said sterilizing material sealed against itself or a sheet of paper coated with a sealing product such as a layer of extruded polyethylene or of poly (vinyl acetate).

23. Package according to claim 19, characterized in that it consists of a rigid container and of a cover formed by the said sterilizing material.

24. The packaging material of claim 1 which has a grammage between 90 and 250 $gm^2$.

25. The packaging material of claim 7 wherein said self-sealing adhesive is a natural rubber adhesive.

26. The packaging material of claim 9 wherein the amount of adhesive deposited ranges between 5 and 10 $g/m^2$.

* * * * *